United States Patent
Plewes

(10) Patent No.: US 6,656,210 B1
(45) Date of Patent: Dec. 2, 2003

(54) THERAPEUTIC HOT/COLD PACK RECEPTACLE AND WRAP

(76) Inventor: Karen L. Plewes, 3002 12th St. Lot #13 Box 306, Harlan, IA (US) 51537

( * ) Notice: Subject to any disclaimer, the term of this patent is extended or adjusted under 35 U.S.C. 154(b) by 0 days.

(21) Appl. No.: 10/006,283

(22) Filed: Dec. 7, 2001

(51) Int. Cl.⁷ .................................................. A61F 7/00
(52) U.S. Cl. ................. 607/112; 607/114; 128/DIG. 15
(58) Field of Search ........................... 607/96, 108, 111, 607/112, 114; 128/DIG. 15

(56) References Cited

U.S. PATENT DOCUMENTS

| | | | | |
|---|---|---|---|---|
| 4,092,982 A | * | 6/1978 | Salem | 604/113 |
| 4,586,506 A | * | 5/1986 | Nangle | 607/112 |
| 4,645,498 A | * | 2/1987 | Kosak | 604/289 |
| 4,676,247 A | * | 6/1987 | Van Cleve | 607/112 |
| 4,688,572 A | * | 8/1987 | Hubbard et al. | 607/112 |
| 5,000,176 A | | 3/1991 | Daniel | |
| 5,020,711 A | | 6/1991 | Kelley | |
| 5,148,804 A | * | 9/1992 | Hill et al. | 607/108 |
| 5,215,080 A | * | 6/1993 | Thomas et al. | 607/112 |
| 5,304,216 A | * | 4/1994 | Wallace | 607/112 |
| 5,409,500 A | | 4/1995 | Dyrek | |
| 5,496,358 A | * | 3/1996 | Rosenwald | 607/108 |
| 5,507,794 A | * | 4/1996 | Allen | 607/112 |
| D371,235 S | | 7/1996 | Robertson | |
| 5,534,021 A | * | 7/1996 | Dvoretzky et al. | 607/112 |
| 5,823,984 A | | 10/1998 | Silverberg | |
| 6,048,326 A | | 4/2000 | Davis et al. | |

* cited by examiner

*Primary Examiner*—Lee Cohen

(57) ABSTRACT

A therapeutic hot/cold pack receptacle and wrap for temporarily securing a hot/cold pack to an injured part of a user's body for the purpose of soothing and healing the injured area. The therapeutic hot/cold pack receptacle and wrap includes a main wrapping member having a plurality of pockets for holding hot/cold packs. The wrapping member being selectively couplable to an injured part of a user's body for the purpose of maintaining contact thereby assuring continuous thermal transference from the hot/cold packs to the inflicted area.

1 Claim, 3 Drawing Sheets

THERAPEUTIC HOT/COLD PACK RECEPTACLE AND WRAP

BACKGROUND OF THE INVENTION

1. Field of the Invention

The present invention relates to therapeutic wraps and more particularly pertains to a new therapeutic hot/cold pack receptacle and wrap for temporarily securing a hot/cold pack to an injured part of a user's body for the purpose of soothing and healing the injured area.

2. Description of the Prior Art

The use of therapeutic wraps is known in the prior art. More specifically, therapeutic wraps heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,000,176; U.S. Pat. No. 5,020,711; U.S. Pat. No. 6,048,326; U.S. Pat. No. 5,409,500; U.S. Pat. No. 5,823,984; and U.S. Pat. No. Des. 371,235.

While these devices fulfill their respective, particular objectives and requirements, the aforementioned patents do not disclose a new therapeutic hot/cold pack receptacle and wrap. The inventive device includes a main wrapping member having a plurality of pockets for holding hot/cold packs. The wrapping member being selectively couplable to an injured part of a user's body for the purpose of maintaining contact thereby assuring continuous thermal transference from the hot/cold packs to the inflicted area.

In these respects, the therapeutic hot/cold pack receptacle and wrap according to the present invention substantially departs from the conventional concepts and designs of the prior art, and in so doing provides an apparatus primarily developed for the purpose of temporarily securing a hot/cold pack to an injured part of a user's body for the purpose of soothing and healing the injured area.

SUMMARY OF THE INVENTION

In view of the foregoing disadvantages inherent in the known types of therapeutic wraps now present in the prior art, the present invention provides a new therapeutic hot/cold pack receptacle and wrap construction wherein the same can be utilized for temporarily securing a hot/cold pack to an injured part of a user's body for the purpose of soothing and healing the injured area.

The general purpose of the present invention, which will be described subsequently in greater detail, is to provide a new therapeutic hot/cold pack receptacle and wrap apparatus and method which has many of the advantages of the therapeutic wraps mentioned heretofore and many novel features that result in a new therapeutic hot/cold pack receptacle and wrap which is not anticipated, rendered obvious, suggested, or even implied by any of the prior art therapeutic wraps, either alone or in any combination thereof.

To attain this, the present invention generally comprises a main wrapping member having a plurality of pockets for holding hot/cold packs. The wrapping member being selectively couplable to an injured part of a user's body for the purpose of maintaining contact thereby assuring continuous thermal transference from the hot/cold packs to the inflicted area.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new therapeutic hot/cold pack receptacle and wrap apparatus and method which has many of the advantages of the therapeutic wraps mentioned heretofore and many novel features that result in a new therapeutic hot/cold pack receptacle and wrap which is not anticipated, rendered obvious, suggested, or even implied by any of the prior art therapeutic wraps, either alone or in any combination thereof.

It is another object of the present invention to provide a new therapeutic hot/cold pack receptacle and wrap which may be easily and efficiently manufactured and marketed.

It is a further object of the present invention to provide a new therapeutic hot/cold pack receptacle and wrap which is of a durable and reliable construction.

An even further object of the present invention is to provide a new therapeutic hot/cold pack receptacle and wrap which is susceptible of a low cost of manufacture with regard to both materials and labor, and which accordingly is then susceptible of low prices of sale to the consuming public, thereby making such therapeutic hot/cold pack receptacle and wrap economically available to the buying public.

Still yet another object of the present invention is to provide a new therapeutic hot/cold pack receptacle and wrap which provides in the apparatuses and methods of the prior art some of the advantages thereof, while simultaneously overcoming some of the disadvantages normally associated therewith.

Still another object of the present invention is to provide a new therapeutic hot/cold pack receptacle and wrap for temporarily securing a hot/cold pack to an injured part of a user's body for the purpose of soothing and healing the injured area.

Yet another object of the present invention is to provide a new therapeutic hot/cold pack receptacle and wrap which includes a main wrapping member having a plurality of pockets for holding hot/cold packs. The wrapping member being selectively couplable to an injured part of a user's body for the purpose of maintaining contact thereby assuring continuous thermal transference from the hot/cold packs to the inflicted area.

Still yet another object of the present invention is to provide a new therapeutic hot/cold pack receptacle and wrap that securely holds a hot or cold pack in place while coupled to the injured body part allowing the user to be mobile.

Even still another object of the present invention is to provide a new therapeutic hot/cold pack receptacle and wrap that would be available in a variety of sizes and shapes to conform to the numerous types of injuries incurred, such as a wrist, elbow, knee, etc.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
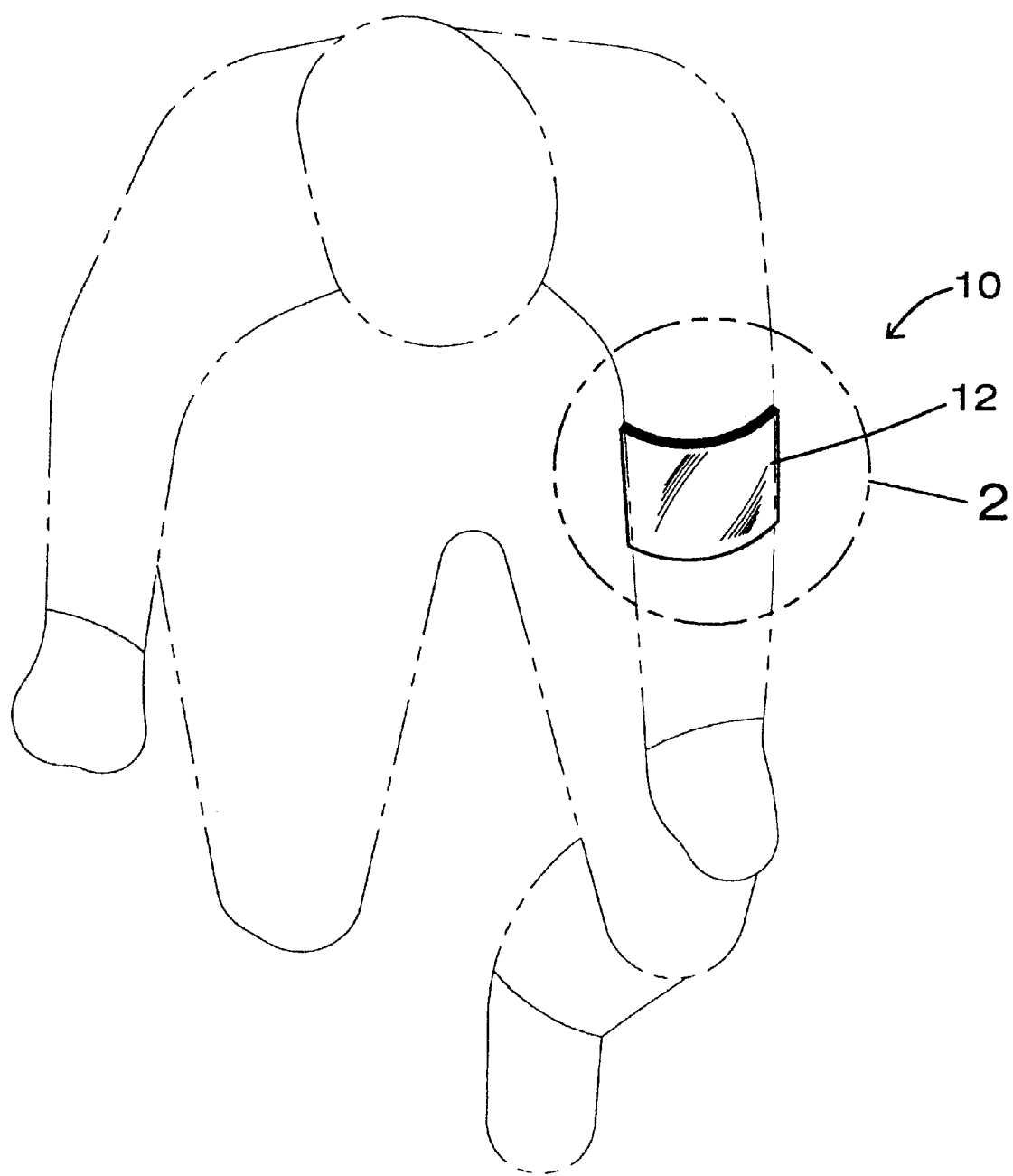
FIG. 1 is a perspective view of a new therapeutic hot/cold pack receptacle and wrap in use according to the present invention.
Figure 2:
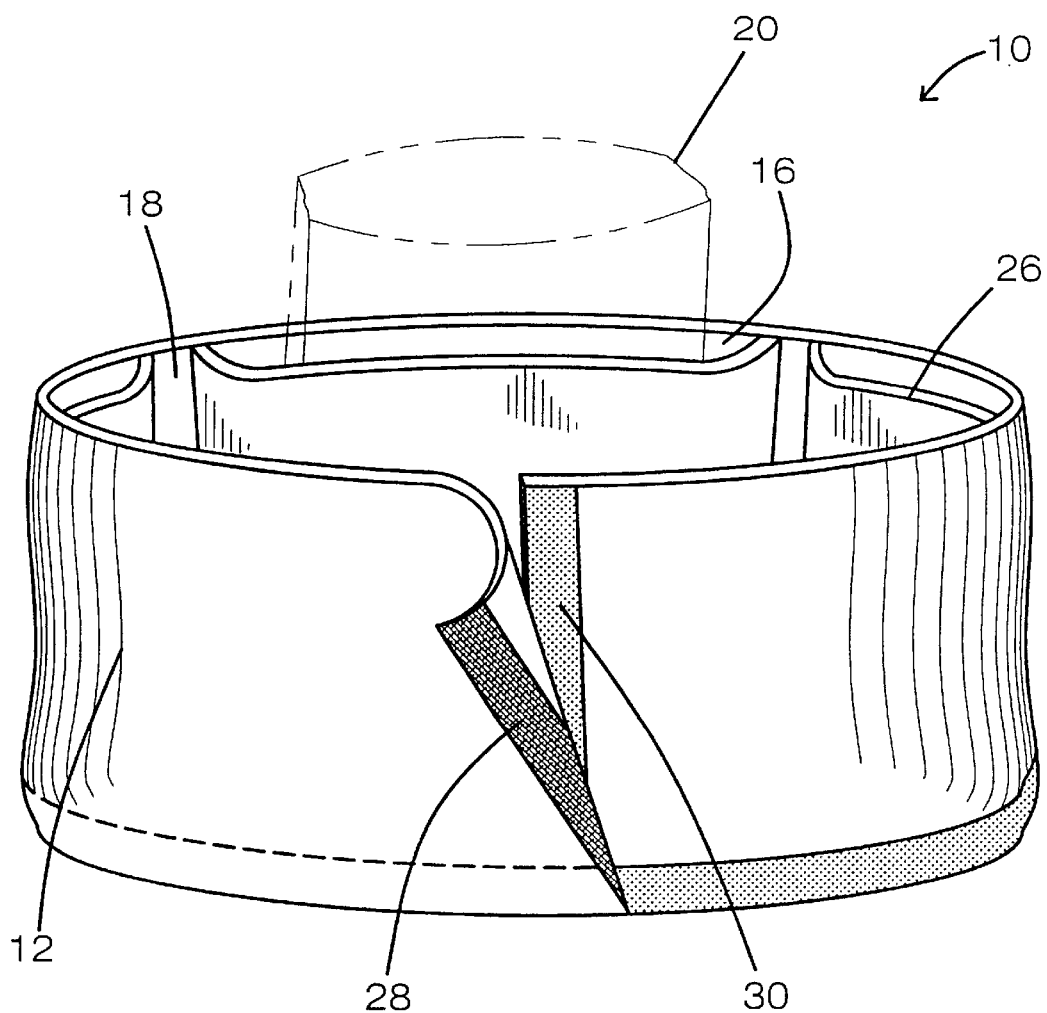
FIG. 2 is a perspective view of the present invention.
Figure 3:
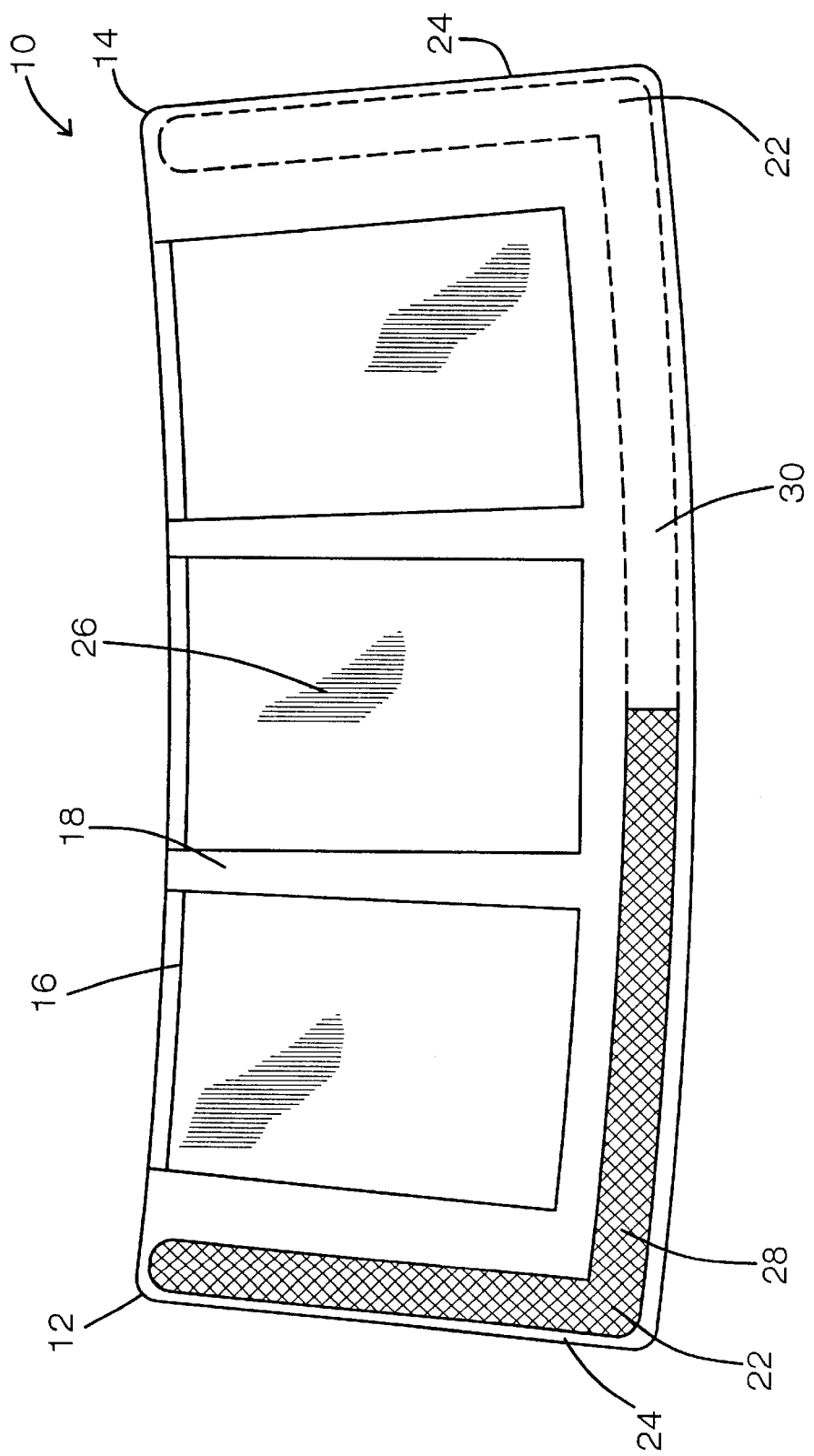
FIG. 3 is a top view of the present invention.

With reference now to the drawings, and in particular to FIGS. 1 through 3 thereof, a new therapeutic hot/cold pack receptacle and wrap embodying the principles and concepts of the present invention and generally designated by the reference numeral 10 will be described.

As best illustrated in FIGS. 1 through 3, the therapeutic hot/cold pack receptacle and wrap 10 generally comprises a main wrapping member 12. The main wrapping member 12 comprises a substantially flat material 14. The main wrapping member 12 has a plurality of pockets 16. The pockets 16 are located on an inner surface 18 of the main wrapping member 12. The pockets 16 are designed for receiving a plurality of hot/cold packs 20.

The main wrapping member 12 has a plurality of fastening portions 22. The fastening portions 22 are positioned proximate perimeter edges 24 of the main wrapping member 12 such that the main wrapping member 12 is designed for encompassing a hurt area on the user's body for the purpose of maintaining contact of the hot/cold pack to the area for therapeutic purposes.

The flat material 14 of the main wrapping member 12 has elastomeric properties for the purpose of conforming to the various areas the main wrapping member 12 is applied.

The plurality of pockets 16 of the main wrapping member 12 is of size and shape so as to conform to a standard hot/cold pack. An inner lining 26 of the pockets 16 comprises a thin material thereby allowing efficient thermal transference from the hot/cold pack to the hurt area.

The plurality of fastening portions 22 comprises a first part of a hook-loop fastener 28 and a second part of a hook-loop fastener 30 such that upon wrapping the main wrapping member 12 around an injured body part, the first and second fastener parts 28, 30 are matable thereby securing the main wrapping member 12 to the user.

The main wrapping member 12 comprises a plurality of shapes and sizes for the purpose of utilization of one of the main wrapping members 12 on a particular body part such as an elbow, knee or other similar area.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A therapeutic hot/cold pack receptacle and wrap for temporarily securing a hot/cold pack to an injured part of a user's body, the therapeutic hot/cold pack receptacle and wrap comprising:

a main wrapping member, said main wrapping member comprising a substantially flat material, said main wrapping member having a plurality of pockets, said pockets being located on an inner surface of said main wrapping member, said pockets being adapted for receiving a plurality of hot/cold packs;

said main wrapping member having a plurality of fastening portions, said fastening portions being positioned proximate perimeter edges of said main wrapping member such that said main wrapping member being adapted for encompassing a hurt area on the user's body for the purpose of maintaining contact of the hot/cold pack to the area for therapeutic purposes;

said flat material of said main wrapping member being elastomeric for conforming to the user's body;

each of said pockets having a bottom positioned in spaced relationship to a bottom edge of said main wrapping member;

each of said fastening portions being generally L-shaped and having a first flange extending proximate a side edge of said main wrapping member, each of said fastening portions further having a second flange extending proximate said bottom edge of said main wrapping member in spaced relationship to each of said pockets and extending between said first flange and a medial portion of said main wrapping member whereby a bottom portion of said main wrapping member is adjustable for securing directly around portion of the user's body adjacent to the hurt area;

said plurality of fastening portions comprising a first part of a hook-loop fastener and a second part of a hook-loop fastener such that upon wrapping said main wrapping member around an injured body part, said first and second fastener parts being matable thereby securing said main wrapping member to the user; and an inner lining of said pockets being a thin material for facilitating efficient thermal transference from the hot/cold pack to the hurt area.

\* \* \* \* \*